United States Patent [19]

Gunderson et al.

[11] Patent Number: 5,439,000
[45] Date of Patent: Aug. 8, 1995

[54] METHOD OF DIAGNOSING TISSUE WITH GUIDEWIRE

[75] Inventors: Richard C. Gunderson, Maple Grove; James S. Sharrow, Bloomington; Jeffrey A. McBroom, Champlin, all of Minn.

[73] Assignee: SpectraScience, Inc., Minneapolis, Minn.

[21] Appl. No.: 154,289

[22] Filed: Nov. 18, 1993

Related U.S. Application Data

[63] Continuation-in-part of Ser. No. 977,985, Nov. 18, 1992, Pat. No. 5,383,467.

[51] Int. Cl.$^6$ ................................ A61B 6/00
[52] U.S. Cl. ................... 128/664; 128/665; 128/634; 604/280; 604/282
[58] Field of Search ............... 128/664, 656–658, 128/665, 633, 634, 772; 606/3, 15; 604/280, 282; 250/227.19; 356/345; 607/92, 93

[56] References Cited

U.S. PATENT DOCUMENTS

| | | |
|---|---|---|
| 3,760,797 | 9/1973 | Stauffer ................... 128/6 |
| 4,171,159 | 10/1979 | White . |
| 4,420,260 | 12/1983 | Martinelli . |
| 4,545,390 | 10/1985 | Leary . |
| 4,554,929 | 11/1985 | Sampson et al. . |
| 4,595,466 | 6/1986 | Ulrich . |
| 4,612,938 | 9/1986 | Dietrich et al. . |
| 4,619,274 | 10/1986 | Morrison . |
| 4,648,892 | 3/1987 | Kittrell et al. . |
| 4,652,129 | 3/1987 | Martinelli . |
| 4,669,465 | 6/1987 | Moore et al. . |
| 4,669,467 | 6/1987 | Willett et al. . |
| 4,718,417 | 1/1988 | Kittrell et al. . |
| 4,721,117 | 1/1988 | Mar et al. . |
| 4,748,986 | 6/1988 | Morrison et al. . |
| 4,796,994 | 1/1989 | Bager . |
| 4,819,632 | 4/1989 | Davies . |
| 4,827,941 | 5/1989 | Taylor et al. ................ 128/657 |
| 4,844,062 | 7/1989 | Wells . |
| 4,873,989 | 10/1989 | Einzig . |
| 4,899,733 | 2/1990 | DeCastro et al. . |
| 4,900,314 | 2/1990 | Quackenbush . |
| 4,921,326 | 5/1990 | Wild et al. ................ 128/6 |
| 4,928,005 | 5/1990 | Lefevre et al. . |
| 4,940,062 | 7/1990 | Hampton et al. ............... 128/657 X |
| 4,958,930 | 9/1990 | Robertson . |
| 4,964,409 | 10/1990 | Tremulis ................. 128/657 |
| 4,969,736 | 11/1990 | Slotwinski . |
| 5,005,584 | 4/1991 | Little . |
| 5,053,033 | 10/1991 | Clarke . |
| 5,094,534 | 3/1992 | Cole et al. . |
| 5,104,392 | 4/1992 | Kittrell et al. . |
| 5,106,387 | 4/1992 | Kittrell et al. . |
| 5,110,211 | 5/1992 | Niki et al. . |
| 5,114,403 | 5/1992 | Clarke et al. . |
| 5,131,380 | 7/1992 | Heller et al. ............ 128/6 |
| 5,133,598 | 7/1992 | Badeau . |
| 5,157,457 | 10/1992 | Taylor . |
| 5,176,149 | 1/1993 | Grenouillet ............ 128/772 |
| 5,188,632 | 2/1993 | Goldenberg ............ 606/15 X |
| 5,196,004 | 3/1993 | Sinofsky . |
| 5,196,005 | 3/1993 | Doiron et al. ............ 606/15 X |
| 5,197,470 | 3/1993 | Helfer et al. . |
| 5,201,317 | 4/1993 | Kanazawa et al. . |
| 5,217,456 | 6/1993 | Narciso, Jr. .............. 606/15 |
| 5,226,423 | 7/1993 | Tenerz et al. ............. 128/772 X |
| 5,267,573 | 12/1993 | Evans et al. ............. 128/772 |
| 5,281,231 | 1/1994 | Rosen et al. ............. 606/15 X |
| 5,295,493 | 3/1994 | Radisch, Jr. ............. 128/772 |
| 5,306,252 | 4/1994 | Yutori et al. ............. 128/772 X |

FOREIGN PATENT DOCUMENTS 0297190 1/1989
0355996 2/1990 European Pat. Off. .
0392987 10/1990 European Pat. Off. .

OTHER PUBLICATIONS

U.S. Statutory Inv. Reg. H637, published Jun. 6, 1989 for "Method and Apparatus for Rapid Optical Phasing" by M. G. Baciak, S/N 857,621, filed Apr. 30, 1986.

Primary Examiner—Lee S. Cohen
Assistant Examiner—Brian L. Casler

[57] ABSTRACT

The present invention provides a guidewire which incorporates an optical fiber and associated diagnostic apparatus for diagnosing tissue in vivo. Use of the present invention provides for diagnosis of tissue and tailoring of the therapeutic portion of the procedure to the tissue or condition identified by the guidewire and associated diagnostic apparatus.

9 Claims, 4 Drawing Sheets

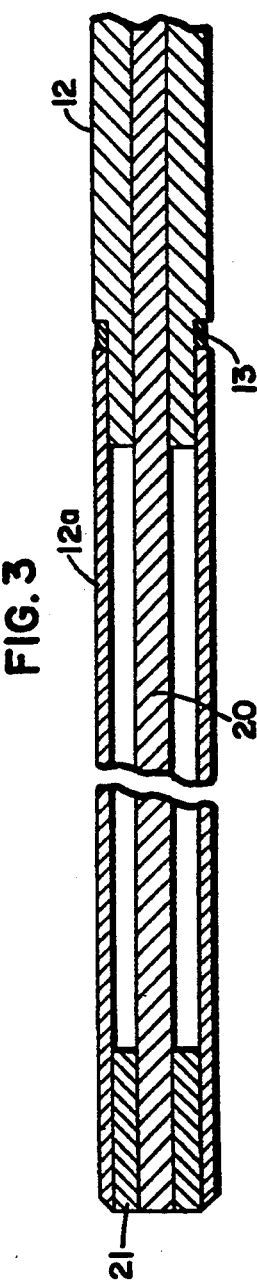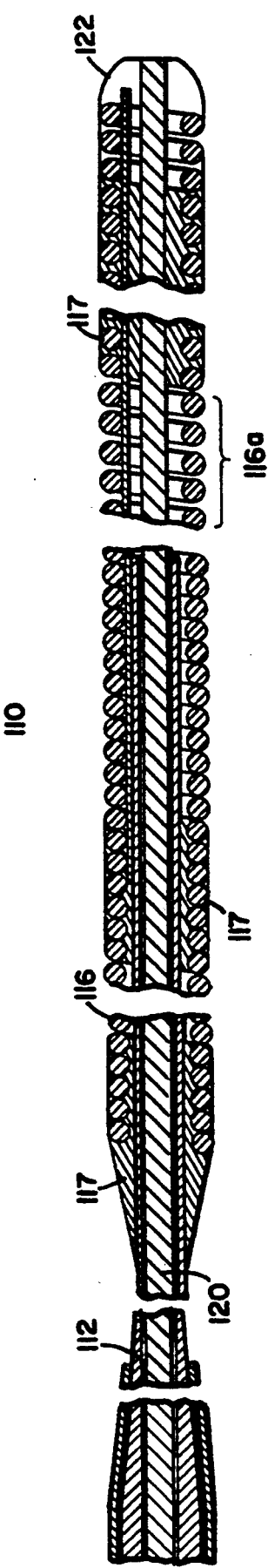

METHOD OF DIAGNOSING TISSUE WITH GUIDEWIRE

RELATED APPLICATIONS

This application is a continuation-in-part of U.S. patent application Ser. No. 07/977,985 filed on Nov. 18, 1992 titled GUIDEWIRE CATHETER AND APPARATUS FOR DIAGNOSTIC IMAGING now U.S. Pat. No. 5,383,467, which is hereby incorporated by reference.

BACKGROUND OF THE INVENTION

1. Field of the Invention

This invention relates to the field of medical diagnosis and treatment. More specifically, the present invention relates to a guidewire device for in vivo tissue diagnosis using electromagnetic energy and methods of using the guidewire device and diagnostic apparatus in conjunction with therapeutic catheters to diagnose and treat tissue in vivo.

2. Description of Related Art

Catheters used to treat and diagnose conditions within patients are known. Examples of such catheters include, but are not limited to, angioplasty catheters incorporating balloons to dilate a vessel, internal drug delivery catheters designed to deliver a drug to a localized area within a patient, laser ablation catheters designed to provide laser radiation within a patient's body for diagnosis and/or treatment, ultrasonic ablation catheters, thermal or mechanical disruptive catheters, stent delivery catheters, catheters for monitoring drug or other chemical concentrations/indications (e.g., pH) in vivo, and catheters for monitoring body functions (e.g., cardiac output).

The majority of catheters are designed to follow a guidewire inserted into the patient and are typically referred to as "over-the-wire" catheters. A subset of those catheters are referred to as "rapid-exchange" catheters. Guidewires are used with catheters because they are typically very flexible and have a smaller diameter than the catheters used for diagnosis and/or treatment. Guidewires are also typically steerable, allowing the physician to better direct the guidewire as it is advanced through the patient. Because of their flexibility, steerability and small diameter, guidewires can be directed to places within a patient that the succeeding catheter could not reach without following the guidewire. In some cases, guidewires can reach locations which no catheter could reach. Guidewires are also typically radiopaque to allow monitoring of their position through standard fluoroscopic techniques.

In use, the guidewire is advanced to the desired position within a patient. In the case of a blood vessel in which a stenosis or occlusion exists, the guidewire is advanced past the stenosis or occlusion and remains in place as the diagnostic and/or therapeutic catheter is advanced to the site of the lesion. The catheter typically contains a lumen, or passageway, through which the guidewire passes as the catheter is advanced along it.

Guidewires are generally known in the art. U.S. Pat. No. 4,545,390 describes a guidewire having a relatively long wire having a proximal end, and a distal end. A relatively short helically wound spring is connected to the distal end which can be bent to retain a curve and is sufficiently flexible to follow a blood vessel without traumatization. The wire is sufficiently torsionally rigid to transmit angular rotation from the proximal end to the distal end to aid in steering the guidewire. In U.S. Pat. NO. 4,554,929 a safety wire interconnects the wire and the coil. In U.S. Pat. No. 4,619,274, a core element decreases in diameter from its proximal end to its distal end, and a helical coil has a diameter that decreases toward its distal end, the coil being formed of a wire whose diameter decrease, with the larger diameter being at the proximal end. In U.S. Pat. No. 4,721,117, a tubular heat-shrinkable jacket covers the wire. In U.S. Pat. 4,748,986, the wire has a tapered intermediate portion, and a flattened distal portion. A coil surrounds the wire, and a safety wire interconnects the wire and the coil.

Catheters containing optical fibers are generally known in the art. U.S. Pat. No. 4,648,892 describes a catheter having an optical shield at the distal end of the catheter. In U.S. Pat. No. 4,669,465, an interlock is provided to prevent operation of a laser until the end of a beam transmitting fiber extends beyond the distal end of the catheter. In U.S. Pat. No. 4,669,467, the ends of a bundle of optical fibers are stressed in order to mix the modes of the optical fibers. Laser catheters are often designed to be introduced over a guidewire which has previously been inserted into a patient.

It is known to analyze radiation that is received from tissue as a result of illumination of the tissue by the use of a catheter. U.S. Pat. No. 4,718,417 describes illuminating tissue with radiation that is generally in the 480 nm range, and then analyzing reflected radiation, generally in the range of 520 to 610 nm, in order to distinguish between healthy tissue and other material, such as plaque. In U.S. Pat. No. 5,104,392, the device operates to continue to ablate a tissue mass until a characteristic returned optical signal is no longer received therefrom. In U.S. Pat. No. 5,106,387, a catheter is used to illuminate a tissue mass to thereby induce fluorescence of the tissue. The returned fluorescence is then analyzed in order to diagnose the tissue mass. All of the above-listed patents are incorporated herein by reference for their teachings relating to diagnosis and treatment of tissue.

One disadvantage of all of the above described systems is the absence of a diagnostic tool to allow the physician to identify the tissue at the treatment site before inserting a separate catheter to diagnose the tissue and/or treat it. The alternative is to eliminate the diagnostic step and provide treatment designed for many different tissues and conditions, but which, in reality, is likely not optimized for any particular tissue or condition.

Another alternative is to provide separate catheters for diagnosis and treatment. That alternative can, however, increase the cost and complexity of the procedure.

Furthermore, exchanging catheters increases the time required to complete the procedures and also increases the risk, or morbidity, associated with the procedure.

Another disadvantage is that some of the known laser catheters are not suited for percutaneous delivery as are most balloon angioplasty and localized drug delivery catheters. As a result, the trauma associated with introducing the catheters is increased over those devices designed for percutaneous administration.

SUMMARY OF THE INVENTION

The present invention provides a guidewire which incorporates an optical fiber and associated diagnostic apparatus for diagnosing tissue in vivo. Use of the present invention provides for diagnosis of tissue and tailoring of the therapeutic portion of the procedure to the tissue or condition identified by the guidewire and associated diagnostic apparatus.

One example of the utility of the invention is in the diagnosis of arterial or vascular obstructions, such as atherosclerotic lesions and thrombi. After identification, the appropriate therapeutic catheter, whether balloon angioplasty, drug delivery or laser ablation, can be advanced along the same guidewire and employed to treat the patient. The present invention is also useful in many other fields including, but not limited to: oncology, urology, gastroenterology, neurosurgery, general surgery, obstetrics/gynecology, etc. It can also be used in laparoscopic procedures for additional diagnostic information, and/or guidance of a therapeutic modality (e.g., laser or cutting/coagulation devices, such as a bipolar electrocautery device).

One preferred embodiment of the guidewire according to the present invention comprises a stainless steel guidewire and an optical fiber which extends through the hollow guidewire. In one preferred embodiment, the major length of the guidewire comprises a thin wall stainless steel tube.

At the distal end of the guidewire, the optical fiber extends through a coil of wire. The terminal end of the guidewire can include an optically clear window, or lens, through which light, or radiation, can be delivered to adjacent tissue from the optical fiber, and by which light can be collected for delivery to the optical fiber, and then to the diagnostic apparatus at the proximal end of the guidewire.

The guidewire preferably includes means for quick connection of the optical fiber within the guidewire to diagnostic apparatus. The ability to quickly disconnect the guidewire from the diagnostic apparatus, remove and/or introduce catheters over the guidewire, and reconnect the guidewire catheter to the diagnostic apparatus offers important advantages.

Diagnosing tissue using a guidewire and diagnostic apparatus according to the present invention allows the physician to choose an appropriate therapeutic catheter with knowledge of the tissue at the treatment site which allows the physician to select the best treatment for the specific type of tissue. Once the appropriate therapeutic catheter is chosen, it can be advanced over the guidewire to the treatment site.

Although some laser catheters may offer the ability to diagnose tissue, laser ablation is not always the most effective or desireable treatment. In such a situation, the laser catheter would need to be removed and a different catheter, e.g., a drug delivery catheter, inserted to treat the tissue. After treatment, the catheter would then be removed and the laser catheter reinserted to provide additional diagnostics.

The present invention would, however, eliminate any need to change between diagnostic and therapeutic catheters and can provide continuous diagnostic capabilities throughout a procedure. As discussed above, the exchange of devices can increase patient morbidity and also leads to increased costs. The present invention can reduce the number of device exchanges required and also reduces the cost of treatment, as a guidewire typically costs one-tenth as much as a typical laser catheter.

Another advantage of the present invention is the ability to provide optically-based diagnostics with percutaneous delivery methods. Percutaneous delivery limits the trauma associated with invasive procedures necessary to introduce many laser catheters into a patient. Many laser catheters do not have the necessary flexibility or are too large for percutaneous administration. As a result, optically-based diagnosis may not be available with known catheters. The guidewire of the present invention is, however, designed for percutaneous administration and can be used with any therapeutic catheter designed for guidewires.

The apparatus and methods used in conjunction with the guidewires according to the present invention preferably employ any number of diagnostic techniques based on electromagnetic energy falling within the infrared to ultraviolet spectrum which can be transmitted by optical fibers. These techniques include, but are not limited to: interference and attenuation across a spectrum (interferometry), induced fluorescence, reflection/absorption spectroscopy, Rayleigh scattering, Raman scattering, and other linear or non-linear optical techniques.

In addition to providing diagnostic information regarding the types of tissue proximate the end of the guidewire, the apparatus and methods according to the present invention, when provided with a plurality of coherent or non-coherent fibers, can be used to provide a two- or three-dimensional image of the area proximate the end of the guidewire.

Other features and advantages of the invention will be apparent to those of skill in the art upon reference to the following detailed description, which description makes reference to the drawing.

BRIEF DESCRIPTION OF THE DRAWING

FIG. 2 is a partial view in cross-section of an alternate preferred guidewire according to the present invention.

FIG. 3 is a partial view in partial cross-section of the proximal end of the guidewire of FIG. 1.

DETAILED DESCRIPTION OF PREFERRED AND ALTERNATE EMBODIMENTS OF THE INVENTION

Figure 1:
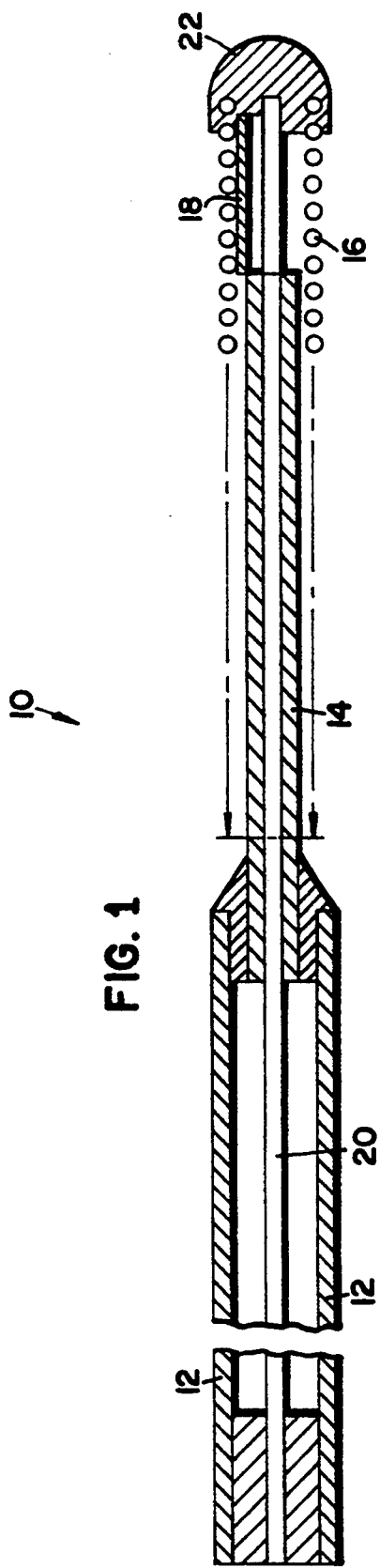
FIG. 1 is a partial view in partial cross-section of one embodiment of a guidewire according to the present invention.

FIG. 1 is a view in partial cross-section of one embodiment of a guidewire constructed according to the present invention. As depicted, the guidewire 10 includes a steerable main tube 12 which extends for a majority of the length of the guidewire 10. The preferred main tube 12 is constructed of thin-walled stainless steel tubing with a maximum outside diameter of less than about 0.038 inch. More preferably the main tube 12 has a maximum outside diameter of less than or equal to about 0.018 inch, and most preferably less than or equal to about 0.014 inch (which is similar to guidewires commonly designed for coronary applications).

By steerable, it is meant that the main tube 12 should transmit rotational force along its length, preferably at a ratio of 1:1. It will also be understood that the main tube 12 should also have enough stiffness to allow it to be advanced through a patient's body. The wire can be manufactured from more than one material and also of materials other than stainless steel including, but not limited to: tantalum, titanium, platinum, nitinol, etc. or alloys thereof.

In the preferred embodiment pictured in FIG. 1, a single optical fiber 20 is contained within the main tube 12. The optical fiber 20 extends past the distal end of the main tube 12, where it is threaded through a second hollow tube 14.

The preferred optical fiber 20 is a single multi-mode optical fiber constructed of a fused silica core and lower refractive index cladding, coated with a polyimide buffer. The core diameter of the preferred fiber 20 is 75 microns, the outer diameter of the cladding is 82 microns and the outer diameter of the buffer is 95 microns. The preferred fiber is available from Polymicro Technologies, Phoenix, Ariz. under the designation P/N 075082095. It is a high index content stepped index optical fiber with a numerical aperture (NA) of 0.22.

Alternatively, it will be understood that any fiber technologies capable of transmitting light of the appropriate wavelengths could be substituted. Examples of substitutes include, but are not limited to: hollow core fibers, dielectric coated fibers, fluid core fibers, and fibers made of exotic glass (e.g., fluoride) and polycrystalline (e.g., metal halide) materials.

Furthermore, it will also be understood that although a single multi-mode fiber is preferred; one single mode fiber or a multiple fiber core arranged in an array (preferably a coherent bundle) wherein input and output ends are arranged with the fibers in a constant pattern, i.e., adjacent fibers at input are also adjacent at output; could be substituted for the preferred single multi-mode fiber. It will be understood that any fiber of fibers substituted for the preferred fiber must also allow the outside diameter of the guidewire 10 to be maintained within the limits described above.

The outside diameter of tube 14 is attached to the inside diameter of wire 12 using a welded or brazed joint or any other suitable method of fastening the tube 14 to wire 12. Welding typically is used to connect tube 14 to wire 12 because the preferred versions of both are fabricated from stainless steel. As with the wire 12, it will be understood that tube 14 could also be fabricated from many other materials including, but not limited to: tantalum, titanium, platinum, nitinol, etc. or alloys thereof.

The optical fiber 20 also extends past the distal end of tube 14 and through the interior of hollow, cylindrical coil 16. Coil 16 is fitted over tube 14 and, as a result, preferably has an inner diameter that is substantially equal to the outer diameter of tube 14.

Coil 16 is preferably attached to tube 14 by at least two solder joints, one located near the wire 12 and the second located at the distal end of tube 14. Solder joints are used in the preferred embodiment because the preferred coil 16 is manufactured from No. 479 platinum alloy. The preferred wire used to form coil 16 has a diameter of 0.002 inches. As with tube 14 and wire 12, it will be understood that coil 16 could also be fabricated from many other materials including, but not limited to: stainless steel, tantalum, titanium, platinum, nitinol, etc. and alloys or combinations thereof. Coil 16 could alternatively be attached to tube 14 by welding, brazing, or adhesives.

The outer diameter of coil 16 is preferably substantially equal to the outer diameter of wire 12. In the preferred embodiment, coil 16 extends over tube 14 up to the transition between wire 12 and tube 14. By extending the coil 16 up to the transition, the outer diameter of guidewire 10 is maintained substantially uniform over its length proximate the distal end of guidewire 10.

In place of the preferred coil 16, it will be understood that other structures which offer a means of providing a flexible, bendable covering for the distal end of guidewire 10 could be substituted for the preferred coil. Examples include, but are not limited to: braided coverings, gooseneck structures, etched tubing, etc.

In the preferred embodiment, the flexibility of the guidewire 10 varies to the most flexible portion proximate its distal end which comprises the optical fiber 20 and coil 16 which extend beyond tube 14. In addition, the distal end of guidewire 10 can preferably be shaped to form a bend which is useful for steering the guidewire 10 through, for example, blood vessels or other tortuous passageways. Providing a bend in the distal end of guidewire 10 can also allow rotational scanning of tissue within the lumen in which the guidewire 10 is located by rotating the proximal end of the guidewire 10. In the preferred embodiment, the distal end of guidewire 10 is capable of being shaped into a curve of 3 millimeters or less inside bend radius without degrading the performance of the optical fiber 20 within guidewire 10.

At the distal end of coil 16 in the preferred embodiment of guidewire 10, the optical fiber 20 terminates and is held in place with a bead of epoxy 22. The epoxy stabilizes the distal end of optical fiber 20 substantially concentric with the end of the coil 16.

Alternately, the distal end of guidewire 10 could terminate in a lens. A lens could serve a number of functions in the guidewire 10. By lens, the present invention is meant to include any and all approximations thereof including, but not limited to: a graded index lens, discrete lens, fiber tip lens, ball-tip lens, etc.

A lens could also function as means for expanding light directed down the optical fiber 20. A lens could be used to expand the light to a diameter at least substantially equal to the outer diameter of coil 16. A lens could also function as means for focusing light striking the distal end of the guidewire 10 on the distal end of the optical fiber 20 for transmission to the proximal end of fiber 20.

Also in one preferred embodiment, the distal end of guidewire 10 is coated with an optically clear elastomer to provide the distal guidewire tip with a soft, flexible and conformable surface that is atraumatic. In addition, guidewire 10 may be covered with a hydrophilic coating(s) to provide increased lubricity and a low friction surface. One preferred coating is PTFE, although it will be appreciated that any other suitable coating could be substituted. The coating can also improve trackability of the guidewire within a lumen or within the guidewire lumen of a catheter. Antithrombogenic coatings could also be applied.

The preferred guidewire 10 also includes a safety wire 18 extending from tube 14 to the distal end of coil 16. Safety wire 18 is provided to ensure the integrity of the assembly forming guidewire 10. In the preferred embodiment, safety wire 18 is formed of stainless steel and is brazed to tube 14 and soldered to coil 16. It will, however, be understood that safety wire could be constructed of many different materials and attached to tube 14 and coil 16 by a variety of methods suitable for the materials used to construct those portions of guidewire 10.

Because the preferred guidewire 10 includes a coil 16 constructed from a platinum alloy, its distal end is radiopaque to standard fluoroscopy techniques to enhance tracking of the device through a patient. Alternate techniques of providing radiopaque markers to in vivo devices, such as using precious metal rings, coatings or other structures, will be well known to those skilled in the art and will not be described further herein.

An alternate preferred construction of a guidewire 110 according to the present invention is depicted in FIG. 2. As shown there, main tube 112 extends over the entire length of main tube 12 and extension tube 14 in the abovedescribed embodiment (see FIG. 1). To accommodate the need for flexibility at the distal end of guidewire 110, the outside diameter of main tube 112 preferably decreases near the distal end of guidewire 110 from a maximum of about 0.014 inches (in one preferred embodiment) to a minimum of about 0.0085 inches.

Preferred coil 116 (constructed similarly to coil 16 described above) is fitted over the distal end of main tube 112 and soldered (or brazed) in place at solder beads 117. Furthermore, coil 116 is preferably pre-stretched at area 116a to relieve tension on the coils which improves flexibility of coil 16. Safety wire 118 (corresponding to safety wire 18 described above) is also provided to insure the integrity of guidewire 110.

Either of guidewires 10 or 110 exhibit the desired operating characteristics of guidewires according to the present invention. For the purposes of the following discussions, it should be assumed that any references to guidewire 10 include guidewire 110 described immediately above.

As a result of its construction, guidewire 10 is capable of following a blood vessel or other body passageway of equal or greater diameter through bends and branches without either turning onto itself, or perforating the passageway. By applying torque or compression to guidewire 10, the guidewire 10 is capable of selective directional advancement through a passageway with little or no trauma.

The preferred embodiment of guidewire 10 described above is designed for use in conjunction with diagnostic apparatus and methods for identifying healthy and diseased tissue through the use of electromagnetic energy falling within the infrared to ultraviolet spectrum which can be transmitted by optical fibers. These techniques include, but are not limited to: interference and attenuation across a spectrum (interferometry), induced fluorescence, reflection/absorption spectroscopy, Rayleigh scattering, Raman scattering, and other linear or non-linear optical techniques.

In addition to providing diagnostic information regarding the types of tissue proximate the end of the guidewire, the apparatus and methods according to the present invention can be used to provide a two- or three-dimensional image of the area proximate the end of the guidewire.

Examples of some, but not all, diagnostic techniques capable of combination with the guidewire 10 according to the present invention are described in U.S. Pat. No. 4,718,417 (Laser Induced Fluorescence); U.S. Pat. No. 5,106,387 (Laser Induced Fluorescence); U.S. Pat. No. 5,125,404 (Spatial Imaging); and U.S. Pat. No. 5,201,318 (Laser Induced Fluorescence & Raman Scattering). Each of the above patents is incorporated by reference for their disclosure regarding methods of diagnosing tissue in vivo with the use of optical fiber based devices.

Guidewires constructed according to the present invention are designed particularly for use in conjunction with therapeutic catheter devices. Examples of such devices include balloon catheters designed to perform percutaneous transluminal coronary angioplasty (PTCA), drug delivery catheters designed to deliver drugs to localized areas within a patient and many other devices designed for introduction into a patient over a guidewire.

Figure 4:
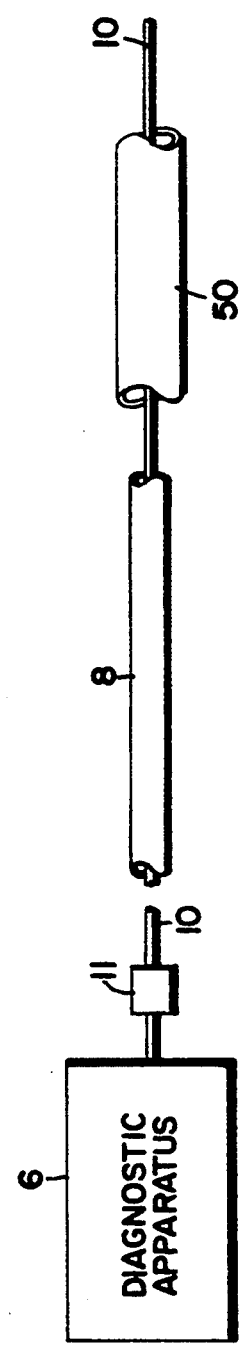
FIG. 4 is a schematic diagram of the guidewire of FIG. 1 connected to diagnostic apparatus and serving as a guide for an over-the-wire catheter.

One procedure using the guidewire 10 of the present invention is depicted in FIG. 4. The guidewire 10 is introduced and advanced to the desired location 50 in a patient. The preferred method of introduction is percutaneously, although other methods of introduction such as through an endoscope operating channel, or through a needle (including a stereotactically-guided probe based on ultrasound, CT or MRI imaging) are also contemplated. The distal end of the guidewire 10 is preferably tracked using fluoroscopy, although guidewires using direct vision (e.g., through an angioscope) could also be employed.

Once in position, the diagnostic system 6 connected to the proximal end of the guidewire 10 through coupling 11 is activated to diagnose the tissue proximate the distal end of the guidewire 10. After the appropriate diagnostic steps are completed and the tissue is identified, the surgeon chooses the appropriate treatment and the therapeutic catheter 8 designed for that treatment.

At that point, the guidewire 10 is uncoupled from the diagnostic system to allow the therapeutic catheter 8 to be introduced over the guidewire 10 (with guidewire 10 being contained within a guidewire lumen of catheter 8). The therapeutic catheter 8 is advanced to the appropriate position to treat the previously diagnosed tissue. It will also be understood that the therapeutic catheter 8 could be introduced over the guidewire 10 earlier in the procedure. In either method, the therapeutic catheter 8 and guidewire 10 can be systematically advanced through the patient to alternately diagnose and treat tissue as needed or to diagnose tissue during treatment to allow guidance of the therapeutic catheter or termination of treatment according to ongoing tissue diagnosis.

One advantage of the present invention is the ability to rapidly and easily exchange different therapeutic catheters to treat tissue with the most efficacious therapy for the conditions diagnosed using guidewire 10. The exchange of catheters is accomplished by uncoupling the guidewire 10 from the diagnostic system, removing the unneeded catheter, replacing it with the desired catheter and coupling the guidewire back to the diagnostic system.

Because of the uncoupling and coupling described above, the preferred guidewire 10 incorporates means for quickly connecting and disconnecting the proximal end of guidewire 10 and the diagnostic apparatus without using conventional optical fiber connector means which are typically larger in diameter than the therapeutic device's guidewire lumen.

In the preferred embodiment, the connection means comprises a quick-connect type coupling 11 (See FIG. 4) at the junction between the proximal end of guidewire 10 and the diagnostic apparatus. The preferred coupling is available from 3M Company, St. Paul, Minn. under the designation FT-350.

When designed for use with the preferred coupling the proximal end of the guidewire 10 terminates with an outside diameter no larger than the outside diameter of the guidewire 10 at any other location along its length to allow guidewire 10 to be inserted through a guidewire lumen in a catheter and be quickly reconnected to the diagnostic apparatus. In the preferred embodiment, that O.D. is 0.014 inches. The fiber 20 is preferably located within the center of the hollow proximal end of guidewire 10 with an accuracy of ±5 μm concentricity.

In one preferred embodiment pictured in FIG. 3, a connection tube 12a is fitted over a section of the proximal end of tube 12 which is provided with a smaller diameter to maintain the overall O.D. of guidewire 10 at 0.014 inches. Connection tube 12a is preferably attached to main tube 12 with epoxy 13, although other means of attaching the tubes can be substituted.

The opposite end of extension tube 12a (forming the proximal end of guidewire 10) is provided with a plug of epoxy to maintain the centering of fiber 20.

The preferred process for providing fiber 20 centered in extension tube 12a involves fixing extension tube 12a and threading fiber 20 through extension tube 12a and maintaining it in position in tension. Fiber 20 can then be repositioned within extension tube 12a using a means for measuring the relative position of the extension tube 12a and the fiber 20. After the desired concentricity is attained, fiber 20 is fixed through the use of epoxy which is wicked into tube 12a as shown in FIG. 3. After epoxy 21 is set, fiber 20 is severed and the proximal end of extension tube 12a is polished to provide the necessary optical interface at coupling 11. It will be understood that other methods of providing extension tube 12a and fiber 20 centered therein can be utilized.

Alternately, it will be understood that the proximal end of guidewire 10 could terminate in main tube 12, with fiber 20 held centered by any suitable method such as epoxy or other centering devices/materials. Extension tube 12a is used in the preferred embodiment to prevent excessive product waste if the desired concentric accuracy is not achieved during the manufacturing process.

Although designed primarily for use with therapeutic catheters, it will be understood that the guidewire and associated diagnostic apparatus could also be used with a catheter designed for combined diagnosis/therapy or a diagnostic catheter. In those situations, the diagnostic capabilities of the present invention could provide additional information based on a different diagnostic technique or the same technique. In either case, the diagnosis of both devices could be compared for verification purposes.

Figure 5:
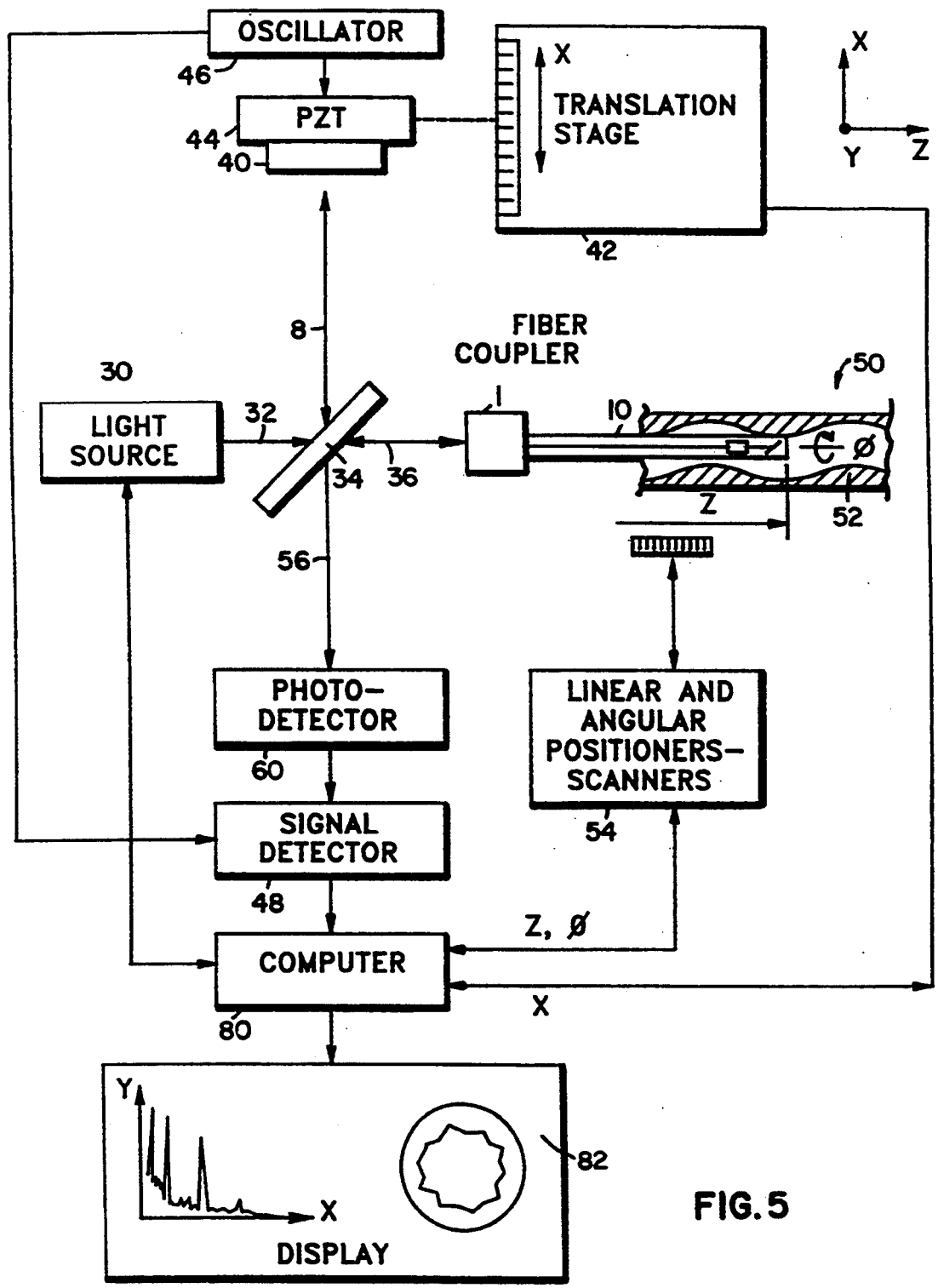
FIG. 5 is a schematic diagram of one diagnostic system designed for use with a guidewire according to the present invention.

FIG. 5 is a schematic diagram of one diagnostic system using interferometry as a diagnostic method in conjunction with a guidewire according to the present invention. Essentially, the apparatus is a form of the Michelson interferometer process.

Although an interferometric method of diagnosis is specifically described herein, this invention should not be construed as limited to the diagnostic technique described below. Rather, the guidewire according to the present invention is designed for use in methods utilizing any optically-based diagnostic techniques including, but not limited to laser induced fluorescence, time-resolved fluorescence, Raman spectroscopy, etc. The following description is provided as only one example of a diagnostic technique useful in the present invention.

The various movements that take place within the system are referenced to a three-dimensional X-Y-Z coordinate system depicted as a part of FIG. 5.

Reference numeral 30 designates a source of electromagnetic energy, such as a laser operating at an exemplary wavelength of about 830 nm, 1300 nm or 1500 nm, a superluminescent diode, or a conventional white light source, a monochromator and an appropriate filter(s) to cover the necessary parts of the optical spectrum. The preferred source produces low coherence energy to facilitate interferometric analyses as discussed below.

One preferred light source 30 comprises a tuneable dye laser working with a line width of about 10 nm, or an array of superluminescent diodes each operating at a different wavelength, or a conventional white light source with a monochromator and appropriate filters to cover the necessary parts of the optical spectrum. Operation of light source 30 is preferably controlled by computer 80.

Light beam output 32 from source 30 is applied to beamsplitter 34. Operation of beamsplitter 34 transmits a first beam 36 into fiber coupler 11, and from there into the proximate end of a guidewire 10 constructed and arranged in accordance with the invention as shown in FIG. 1. Operation of beamsplitter 34 also causes a second beam 38 to be directed upward into a movable reference mirror 40.

Mirror 40 is physically movable in the X direction by operation of a translation stage 42, under the control of computer 80. In addition, the present X position of mirror 40 is continuously provided as an input signal to computer 80. The X position of mirror 40 can be dithered (i.e., moved back and forth a small amount in the X direction) about the command X position by operation of piezoelectric movement transducer (PZT) 44, under the control of oscillator 46. The output of oscillator 46 is also preferably connected as an input to heterodyne signal detector 48.

The effects of 1/f noise can be avoided by dithering the position of mirror 40 at each discrete X position of mirror 40 due to operation of PZT transducer 44.

Reference numeral 50 designates a section of an artery within which the distal end of guidewire 10 is positioned. As shown, vessel 50 includes an internal tissue mass 52. A linear and/or angular positioner/scanner 54 operates to control the Z position of distal end of the guidewire 10 along vessel 50, and also may cause the viewing direction of distal end of guidewire 10 to rotate in the X-Y plane. Positioner/scanner 54 is also preferably controlled by computer 80.

In the operation of the system depicted in FIG. 5, a beam of laser energy emanates from guidewire 10 and impinges upon tissue mass 52. The energy is reflected back to the guidewire 10 and its optical fiber which then transmits the returning radiation to beamsplitter 34. In addition, a reference beam is reflected from mirror 40. This beam is also presented to beamsplitter 34.

These two beams, one beam being an X position reference beam and the other a beam containing information relative to tissue mass 52 for the present Z position of distal end of guidewire 10 combine or interfere at beamsplitter 34. As a result, an interference pattern beam 56 (i.e., an output beam) is presented to photodetector 60. The output of detector 60 is presented as a second input to signal detector 48.

The mirror 40 is moved to change, or scan, the path length of the reference beam in a known manner. This provides a known reference to the distance inside of the tissue 52 from which returned radiation is being received. More specifically, the path length of the reference beam is changed by changing the position of the movable mirror 40. Each given position of the mirror 40 provides an accurate correlation to the point, or position, inside of the tissue 52 from which the reflected signal is being currently sampled.

Only light that is reflected, or scattered, from tissue sites that are spaced from the beamsplitter 34 exactly the same optical distance as the movable reference mirror 40 is spaced from the beamsplitter 34 will produce constructive interference with the reference beam, and thus give an interferometer signal that is proportional to both the amplitude of the reflected signal, and the amplitude of the reference beam.

The output from signal detector 48 is provided as an additional input to computer 80 which operates to drive a display output 82 whereat the X-Y plane configuration of vessel 50 can be displayed, and wherein the amplitude of the interference signal is plotted as the Y coordinate, and as a variable function of the X position of the distal end of the guidewire 10 within vessel 50.

Figure 6:
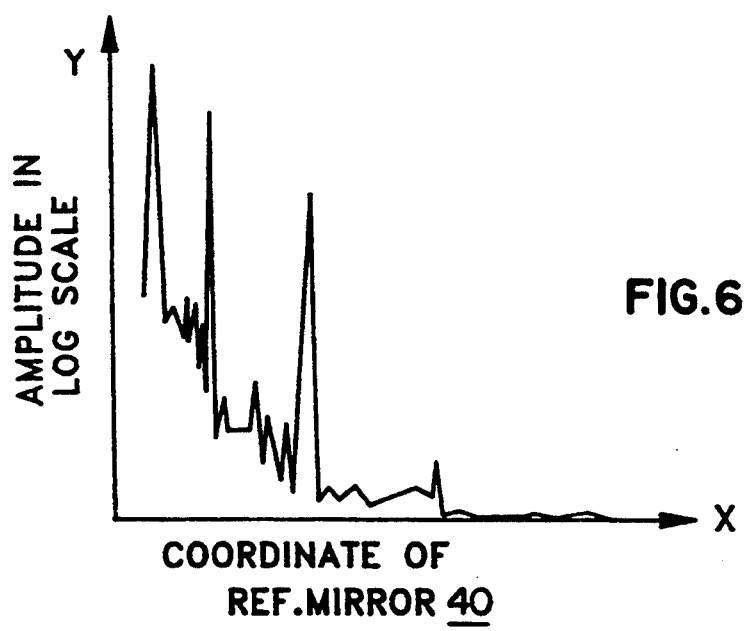
FIG. 6 is a hypothetical representative output display provided by the diagnostic system of FIG. 5.

FIG. 6 shows such a signal plot wherein the signal amplitude (the Y axis) of one hypothetical example is plotted in a logarithmic scale. The spikes present in the signal plot, or curve, represent discontinuities in tissue mass 52. The average slope of this signal plot between adjacent signal spikes represents the average extinction coefficient for that given part of tissue mass 52.

The plot of FIG. 6 is a function of various mirror positions, and thus various distances inside of the tissue 52. As a result, the plot of FIG. 6 provides information as to both the nature and the geometry of the tissue 52.

Attenuation of incident light beam 36 by tissue mass 52, characterized as the tissue's coefficient of total attenuation, is determined by absorption and scattering of the guidewire 10 generated light by tissue mass 52. Since this coefficient is somewhat a function of the wavelength of the incident light, use of a low coherence light source that is tuneable to different wavelengths, or is workable at a number of wavelengths simultaneously, enhances identification of tissue mass 52 by providing attenuation characteristics best suited to each type of tissue likely to be encountered.

Attenuation of incident light is determined by absorption and scattering of the light by the tissue 52. This attenuation effect is characterized as the coefficient of total attenuation. This coefficient is of an inherent value for each given tissue medium. In other words, this coefficient is a tissue "fingerprint" that is significantly different for different types of atherosclerotic plaque and thrombi, and can be used for tissue identification.

Because this coefficient is somewhat a function of the wavelength of the incident light, use of a low coherence light source that is tuneable to different wavelengths, or is workable at a number of wavelengths simultaneously, enhances tissue identification.

Figure 7:
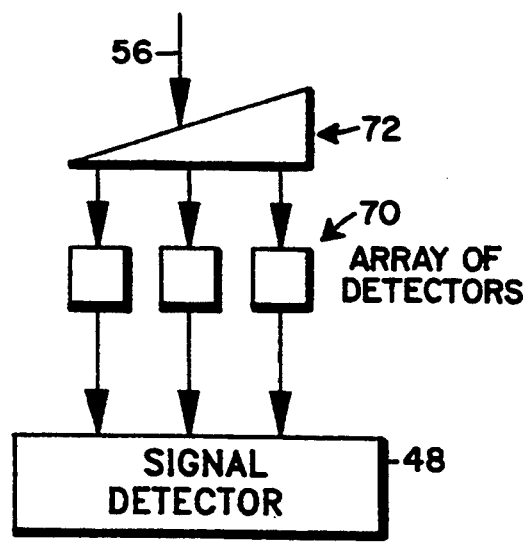
FIG. 7 is a schematic representation of one embodiment of separating a plurality of wavelengths in the diagnostic system of FIG. 5.

To distinguish the signals corresponding to each wavelength when using a light source that is capable of simultaneously operating at a plurality of wavelengths, an array of photodetectors 70 is used, as shown in FIG. 7. In the preferred system, one photodetector is provided for each wavelength, with a grating or similar light dispersion element 72 in front of array 70 to disperse the wavelengths to the photodetectors. Other means of separating and measuring the radiation will be known to those skilled in the art.

While the invention has been described by making reference to various embodiments thereof, it is known that those skilled in the art will, upon learning of the invention, readily visualize yet other embodiments that are within the spirit and scope of the invention. Thus, it is intended that the foregoing description not be taken as a limitation on the invention.

We claim:

1. A method of diagnosing and treating tissue in vivo comprising the steps of:
    a) inserting a guidewire into a patient, the guidewire comprising a hollow guidewire tube having proximal and distal ends, flexible means attached to the distal end of the guidewire tube for providing flexibility at the distal end of the guidewire, the flexible means forming a hollow bore; and an optical fiber having proximal and distal ends, the optical fiber contained within the hollow guidewire tube and extending through the hollow bore of the flexible means to the distal end of the guidewire;
    b) advancing the distal end of the guidewire to a position proximate the tissue;
    c) illuminating the tissue with electromagnetic radiation transmitted through the optical fiber from the proximal to the distal end of the guidewire;
    d) returning electromagnetic radiation from the tissue through the optical fiber to the proximal end of the guidewire; and
    e) diagnosing the tissue based on the electromagnetic radiation transmitted and returned through the guidewire.

2. The method of claim 1, further comprising the step of advancing a catheter over the guidewire to a position proximate the tissue.

3. The method of claim 2, further comprising the steps of:
    a) disconnecting the guidewire from a diagnostic apparatus used to perform the diagnosing step before the step of advancing the catheter; and
    b) reconnecting the guidewire to the diagnostic apparatus.

4. The method of claim 1 further comprising the step of treating the tissue based on information from the diagnosing step.

5. The method according to claim 4, the step of treating further comprises advancing a catheter over the guidewire.

6. The method according to claim 5, further comprising the step of disconnecting the guidewire from a diagnostic apparatus used for the step of illuminating the tissue before advancing the catheter over the guidewire.

7. The method according to claim 6, further comprising the step of reconnecting the guidewire to the diagnostic apparatus after advancing the catheter over the guidewire.

8. The method according to claim 7, further comprising the step of
    a) reconnecting the guidewire to the diagnostic apparatus; and
    b) diagnosing the tissue after the step of treating.

9. A method of diagnosing and treating tissue in vivo comprising the steps of:
    a) inserting a guidewire into a patient, the guidewire comprising a hollow guidewire tube having proximal and distal ends, flexible means attached to the distal end of the guidewire tube for providing flexibility at the distal end of the guidewire, the flexible means forming a hollow bore; and an optical fiber having proximal and distal ends, the optical fiber contained within the hollow guidewire tube and extending through the hollow bore of the flexible means to the distal end of the guidewire;

b) advancing the distal end of the guidewire to a position proximate the tissue;

c) illuminating the tissue with electromagnetic radiation transmitted through the optical fiber from the proximal to the distal end of the guidewire;

d) returning electromagnetic radiation from the tissue through the optical fiber to the proximal end of the guidewire;

e) diagnosing the tissue based on the electromagnetic radiation transmitted and returned through the guidewire;

f) advancing a catheter over the guidewire to a position proximate the tissue; and g) treating the tissue with the catheter based on information from the diagnosing step.

* * * * *